United States Patent [19]

Marks

[11] Patent Number: 4,548,211
[45] Date of Patent: Oct. 22, 1985

[54] COMPUTER ASSISTED ADMITTANCE PLETHYSMOGRAPH

[76] Inventor: Lloyd A. Marks, 21 Bridge Rd., Setauket, N.Y. 11733

[21] Appl. No.: 570,079

[22] Filed: Jan. 12, 1984

[51] Int. Cl.$^4$ .............................................. A61B 5/02
[52] U.S. Cl. .................................... 128/694; 128/693
[58] Field of Search ................................ 128/693, 694

[56] References Cited

U.S. PATENT DOCUMENTS

| | | | |
|---|---|---|---|
| 3,149,627 | 9/1964 | Bagno | 128/693 |
| 3,570,474 | 3/1971 | Jonson | 128/694 |
| 3,742,936 | 7/1973 | Blanie et al. | 128/693 |
| 3,835,839 | 9/1974 | Brown | 128/693 |
| 3,835,840 | 9/1974 | Mount | 128/693 |
| 3,847,142 | 11/1974 | Williams et al. | 128/694 |
| 4,204,545 | 3/1980 | Yamakoshi | 128/693 |
| 4,205,688 | 6/1980 | Hauser et al. | 128/694 |
| 4,258,720 | 3/1981 | Flowers | 128/694 |
| 4,432,374 | 2/1984 | Osanai | 128/694 |
| 4,437,469 | 3/1984 | Djordjevich et al. | 128/693 |

Primary Examiner—Arthur P. Demers
Attorney, Agent, or Firm—Wigman & Cohen

[57] ABSTRACT

An improved method and apparatus for measuring the pulsatile volume and net inflow in a body segment (e.g. a limb) is disclosed. An amplitude stabilized oscillator of high quality is utilized, together with normalization of the output signal measured at the body segment relative to the input signal delivered to the body segment such that an improved signal-to-noise ratio is achieved. In addition, utilizing a digital computer and an EKG signal as a time reference, the individual plethysmograph volume pulse and its first derivative are selectively averaged over many beats, thus further improving the signal-to-noise ratio and allowing a more critical examination of the wave profile. The outputs from the computer include the plethysmogram, the first and second derivatives thereof, the averaged EKG waveform, and the absolute physiologic values of peak-to-peak pulsatile volume, and peak net inflow.

28 Claims, 7 Drawing Figures

| VOLUME PULSE | FLOW PULSE | DATE | TIME | GRAPHIC FLOW Decreased ← → Increased |
|---|---|---|---|---|
| 145 MICL | 3654 MICL/SEC | 10/27 | 09:54 | * |
| 145 MICL | 3298 MICL/SEC | 10/27 | 09:54 | * |
| 132 MICL | 3578 MICL/SEC | 10/27 | 09:55 | * |
| 146 MICL | 3600 MICL/SEC | 10/27 | 09:56 | * |
| 157 MICL | 4020 MICL/SEC | 10/27 | 09:57 | * |
| 146 MICL | 3956 MICL/SEC | 10/27 | 09:58 | * |
| 145 MICL | 3848 MICL/SEC | 10/27 | 09:58 | * |
| 148 MICL | 3934 MICL/SEC | 10/27 | 09:59 | * |
| 146 MICL | 3783 MICL/SEC | 10/27 | 10:00 | * |
| 141 MICL | 3610 MICL/SEC | 10/27 | 10:01 | * |
| 145 MICL | 3783 MICL/SEC | 10/27 | 10:01 | * |
| 150 MICL | 4063 MICL/SEC | 10/27 | 10:02 | * |
| 106 MICL | 2478 MICL/SEC | 10/27 | 10:04 | A→*  |
| 170 MICL | 4862 MICL/SEC | 10/27 | 10:04 | * |
| 170 MICL | 4042 MICL/SEC | 10/27 | 10:05 | * |
| 164 MICL | 4236 MICL/SEC | 10/27 | 10:06 | * |
| 172 MICL | 4409 MICL/SEC | 10/27 | 10:07 | * |
| 162 MICL | 4376 MICL/SEC | 10/27 | 10:08 | * |
| 159 MICL | 4463 MICL/SEC | 10/27 | 10:08 | * |
| 158 MICL | 4430 MICL/SEC | 10/27 | 10:09 | * |
| 155 MICL | 4537 MICL/SEC | 10/27 | 10:10 | * |
| 158 MICL | 4322 MICL/SEC | 10/27 | 10:11 | * |
| 146 MICL | 3902 MICL/SEC | 10/27 | 10:12 | * |
| 144 MICL | 3977 MICL/SEC | 10/27 | 10:13 | * |
| 142 MICL | 4096 MICL/SEC | 10/27 | 10:13 | * |
| 121 MICL | 2780 MICL/SEC | 10/27 | 10:14 | * |
| 70 MICL | 1949 MICL/SEC | 10/27 | 10:15 | B→* |
| 143 MICL | 3999 MICL/SEC | 10/27 | 10:16 | * |
| 136 MICL | 3643 MICL/SEC | 10/27 | 10:17 | * |
| 156 MICL | 4225 MICL/SEC | 10/27 | 10:18 | * |
| 165 MICL | 4484 MICL/SEC | 10/27 | 10:18 | * |
| 159 MICL | 4117 MICL/SEC | 10/27 | 10:19 | * |
| 154 MICL | 4107 MICL/SEC | 10/27 | 10:20 | * |
| 159 MICL | 4473 MICL/SEC | 10/27 | 10:21 | * |
| 159 MICL | 4290 MICL/SEC | 10/27 | 10:22 | * |
| 162 MICL | 4258 MICL/SEC | 10/27 | 10:22 | * |
| 156 MICL | 4268 MICL/SEC | 10/27 | 10:23 | * |
| 159 MICL | 4376 MICL/SEC | 10/27 | 10:24 | * |
| 161 MICL | 4657 MICL/SEC | 10/27 | 10:25 | * |
| 166 MICL | 4214 MICL/SEC | 10/27 | 10:26 | * |

*FIG. 7*

COMPUTER ASSISTED ADMITTANCE PLETHYSMOGRAPH

BACKGROUND OF THE INVENTION

The present invention relates generally to the measurement of the pulsatile volume and net inflow of fluids in body segments and an analysis of those measurements. More particularly, the present invention relates to the measurement of pulsatile volume and net inflow of blood in the limb of a human, by non-invasive electrical means, and the analysis of that data, together with other physiological data, to enhance the reproducibility and signal-to-noise characteristics of those measurements.

The measurement of peripheral blood flow is important in medicine since there are many specific diseases in which peripheral blood flow is impaired, e.g. diabetes and atherosclerosis. Also, the peripheral blood flow is altered as the total cardiac output is increased or decreased. Thus cardiac output is particularly important in patients who are under anesthesia, are in the post-operative state, or are critically ill or unstable. As blood flow from the heart falls, the peripheral blood flow is dramatically reduced to preserve flow to the brain and vital organs.

Blood flow to an extremity can be measured painstakingly and invasively by dissecting out the main blood vessels to the limb (e.g. brachial artery in an arm) and encircling it with an electromagnetic flow probe. That is clearly not a technique suitable for clinical use. Currently, no means are available for directly measuring peripheral blood flow non-invasively.

The measurement of peripheral blood flow has therefore relied upon techniques which require theoretical assumptions which allow an approximation or calculation of flow from other data which may be obtained non-invasively. The most commonly used techniques involve the calculation of flow from changes in limb volume, a measurement which can be obtained non-invasively. The measurement of volume is referred to as "plethysmography", and includes a variety of techniques including displacement of liquids and gases, and the stretching of mechanical or electrical strain gauges. The present device relates to the family of electrical impedance or admittance plethysmographs in which the body segment itself is an electrical conductor whose properties are altered as it changes in size throughout the cardiac cycle, as blood enters and leaves the body segment.

A change in volume of a body segment may be calculated as follows:

$$\Delta V = \rho \left( \frac{L}{Z_o} \right)^2 \Delta Z \text{ (Nyboer's Equation)};$$

where
V = the change in volume of the body segment;
L = the length between the inner measuring electrodes (or length of the body segment);
$Z_0$ = the baseline impedance;
$\rho$ = the resistivity of the blood; and
$\Delta Z$ = the change in impedance which occurs as the limb or body segment changes size during the cardiac cycle.

By differentiating:

$$\frac{dV}{dt} = \rho \left( \frac{L}{Z_o} \right)^2 \frac{dZ}{dt},$$

where:
dV/dt = the change in volume per unit (or net inflow into the body segment); and
dZ/dt = the rate of change of the impedance.

This formula requires measurement of $Z_0$, and assumes that $Z_0$ remains relatively constant throughout the measurement period. That equation may be rearranged as follows:

$$\Delta V = \rho L^2 \Delta Y$$

where Y is the change in admittance. Differentiating:

$$dV/dt = \rho L^2 \,(dY/dt)$$

where (dY/dt) is the rate of change of the admittance. This approach is attractive because the addition or subtraction of blood to the limb or body segment is treated mathematically as the addition or removal of a parallel conductor (blood) to a baseline conductance (the limb or body segment tissue) and there is no need to include that baseline in the calculation.

As stated earlier, no known direct non-invasive technique exists to measure peripheral flow. One technique which has been used over the years and with many different devices is that of venous occlusion plethysmography. By inflating a cuff proximal to the limb segment at a pressure higher than the typical venous pressure, yet lower than the diastolic arterial pressure, it is assumed that the compliant veins will act as a reservoir and expand in volume at the rate of arterial inflow. That technique assumes infinite distensibility of the vein over the first few cardiac cycles post-occlusion and no alteration of arterial inflow due to a low pressure cuff inflation. After a number of cardiac cycles, the venous pressure rises and ultimately exceeds the cuff pressure. The early rate of rise of the volume curve as generated by a plethysmograph is assumed to equal the arterial inflow.

A different approach is to examine the pulsatile volume change and net inflow (or rate of volume change) that occurs within each cardiac cycle, without application of occlusion. The constant component of flow is ignored and instead, the focus is on the pulsatile component. That approach relies upon the assumption that total flow varies with pulsatile flow. Although that introduces theoretical inaccuracies into the absolute measurement of flow, it does preserve the ability to follow changes and trends in flow. The admittance technique has not yet been applied to that type of measurement.

When measuring pulsatile flow, since the body segment volume changes less than 0.05% with each cardiac cycle, such technique is severely limited by the signal-to-noise characteristics of the electronic device used. Furthermore, there is considerable beat-to-beat variability of the peripheral volume pulse making that measurement difficult to reproduce.

The volume of an electrical conductor may be determined from its electrical conductance. At high frequencies (e.g. between 20 and 100 kilohertz), biological tissues behave essentially as pure conductors. That principle may be used to measure volume changes occurring in a body segment. Such a technique, usually referred to as "electrical admittance (or impedance) plethysmography," has been used to estimate peripheral limb or body segment flow utilizing the venous occlusion method described above. That method involves the use of a cuff, which is attached around the limb whose flow is to be monitored, and then inflated in order to occlude the venous blood flow in that limb.

One such device which utilizes the venous occlusion method for measuring blood flow rate non-invasively is disclosed in U.S. Pat. No. 4,204,545, to Yamakoshi. In that device, the initial admittance value of the limb is measured and then the venous return in the limb to be examined is occluded. The initial admittance value of the limb is held, and then compared with the subsequent admittance value of the limb due to the venous occlusion. The device of Yamakoshi utilizes an automatic cuff to accomplish the venous occlusion and four electrodes spaced apart on the limb to be examined. A high-frequency, very small current is supplied to the limb segment and the limb blood flow is measured as a change in the electrical admittance of the limb segment caused by the venous occlusion. While that method enables a non-invasive measurement of blood flow, the device disclosed therein erroneously assumes that the output amplitude of the input current device remains constant.

While Yamakoshi has applied the admittance technique and an automatic cuff inflation device to the computation of venous occlusion plethysmograms, he has computed admittance simply by taking the reciprocal of impedance and assumed that the exciting voltage was accurate and non-varying. Because the venous occlusion method utilizes relatively large pooling phenomenon, and relies upon a straight line approximation to a volume curve which has superimposed pulsatile components, the precise measurement of small volume changes is not imperative when using that technique.

An impedance plethysmograph in which an analog computer is used in order to compute the blood flow from the measured blood volume changes is disclosed in U.S. Pat. No. 3,835,839, to Brown. In that patent, a flow rate computer is disclosed which operates with an impedance plethysmograph of the type having current and voltage electrodes which are applied to a selected biological segment. Plethysmograph outputs are generated which are proportional to tissue conductance within the segment being examined, the deviation from the basic resistance of the segment and the rate of change of that deviation. The computer analyzes such signals and, together with constants of proportionality injected into the circuit at appropriate points, provides an output in units of absolute flow rate per unit of time.

Since limb admittance varies less than 0.05% during the cardiac cycle, that rather small change causes the extraction of the signal from the background noise to be a technically difficult problem. Thus, the use of the limb admittance (or impedance) plethysmogram has been almost exclusively limited to the venous occlusion technique described by Yamakoshi, and others, in which relatively large volume changes occur over multiple beats.

However, in order to provide a more accurate peripheral volume pulse measurement than the prior art, such as the Brown device, the instant admittance plethysmograph was developed. By improving the signal-to-noise ratio utilizing field effect transistor circuitry to stabilize the signal source and an analog divider in order to correct for fluctuations of the input amplitude, the instant device provides an improved and accurate means for measuring the peripheral limb pulsatile volume and net inflow. Details of the individual volume pulse wave measured by the instant admittance plethysmograph are clarified by signal averaging, utilizing a digital computer system.

SUMMARY AND OBJECTS OF THE INVENTION

In view of the foregoing, it should be apparent that there still exists a need in the art for a method of and an apparatus for accurately measuring the pulsatile volume and net inflow in a limb or body segment of a human in which non-invasive electronic means are utilized in a simple and precise manner to produce an electrical signal representative of such parameters and in which a general purpose digital computer is utilized to analyze and further clarify those signals representative of peripheral blood flow dynamics. It is, therefore, a primary object of this invention to provide a method of and an apparatus for measuring the peripheral limb pulsatile volume and net inflow of a body segment by non-invasive electrical means which is characterized by simple yet accurate electronic circuitry and which produces an accurate representation of the pulsatile volume and net inflow to be measured.

More particularly, it is an object of this invention to provide an admittance plethysmograph apparatus as aforementioned having simple and reliable electronic circuitry which provides an improved signal-to-noise ratio and correction for fluctuations of the excitation input amplitude.

Another object of the present invention is to provide reliable and relatively inexpensive excitation stabilization circuitry for use in reducing the signal-to-noise ratio in an admittance plethysmograph.

A further object of the present invention is to provide a method of reducing the signal-to-noise ratio of an admittance plethysmograph wherein the excitation signal source is stabilized and provision is made to correct for the fluctuations of the input amplitude for the source.

Another object of the present invention is to provide an accurate analysis of the peripheral blood flow of a human utilizing a digital computer system wherein the individual volume pulse signal, its first derivative, and the total limb segment conductivity signals, as well as an electrocardiagram signal (EKG) are provided as inputs to the computer which then generates the desired pulse wave amplitude information.

Another object of the present invention is to provide computer analysis in a compact package that can deliver that information at the bedside of a patient if necessary.

Furthermore it is another object of this invention to provide an analog-to-digital converter and digital signal processing to enhance the reproducibility of the measurements. That is accomplished by selecting beats which satisfy acceptable noise criteria and averaging those acceptable beats over a plurality of cardiac cycles using the QRS complex of the EKG as a time reference.

It is yet another object of this invention to provide a digitally derived second derivative of the plethysmograph volume pulse.

It is an object of this invention to utilize a computer to generate from those processed beats, measurements to include but not exclusively, the peak-to-peak amplitude of the pulse volume, the peak value of the first derivative of the pulse volume (peak net inflow), and the time from the QRS onset to the peak net inflow.

Furthermore, it is still another object of this invention to enable the reset of the measurement cycle automatically, and thus provide the above measurements over and over again, thus acting as a real time pulsatile volume and net inflow monitor.

It is yet another object of this invention to provide useful measurements related to peripheral blood flow which do not require the application of a cuff, or the intervention of a technician but which may be continuously provided in an ongoing fashion without constant or even occasional attention by hospital personnel.

Furthermore it is an object of this invention to continuously monitor the baseline conductance of a body segment and store that value in a digital computer for computational purposes.

It is still another object of this device to convert all of the aforementioned conductance and first derivative of conductance values into physiologic values of volume (which may be measured in microliters) and net inflow (which may be measured in microliters per second), by applying suitable algorithms to those raw values, the hematocrit, and the length between the electrodes. Rho ( ) or resistivity is computed from the hematocrit by use of a regression equation.

Furthermore, it is an object of this device to provide computer algorithms which may combine the above measurements with one another or with patient demographic data such as body weight, proximal and digital limb segment circumference and height, to provide useful derived parameters. Those parameters may include, although not exclusively, body surface area, limb volume, limb impedance, tissue resistivity, normalization of pulse volume and net inflow to body surface area to body weight, to limb volume, to baseline volume, to segment length, to segment length and unit weight, to segment length and unit body surface area, and normalization of QRS-peak net inflow interval to body height.

Briefly described, those and other objects of the invention are accomplished in accordance with its apparatus aspects by providing an admittance plethysmograph which utilizes a tetrapolar electrode system, a high quality amplitude stabilized oscillater as an exciter, amplitude normalization to improve the signal-to-noise ratio, and a digital computer. That system allows the examination of the profile of the individual volume pulse, its first derivative, and the total limb segment conductivity. The oscillator in the preferred embodiment provides a 47 kilohertz output signal, at 1 milliamp, and achieves stability by using a high quality amplitude stabilized oscillator as the exciting source, rather than assuming the stability of the source. The amplitude stabilization may be achieved by an FET (field effect transistor) feedback circuit.

Constant current amplitude may be delivered to the limb more effectively by using an op-amp voltage-to-current converter, rather than a voltage source delivered through an impedance which is large relative to the limb. (That is the common technique used for application of current in typical impedance plethysmography).

The output voltage signal of that oscillator is converted to a current signal, which current signal is peak detected and then divided by the peak of the body segment output voltage signal, thus correcting for fluctuations of the output amplitude of the oscillator. Alternatively, other analog means, such as a root-mean-square detector, may be used to provide signals which are proportional to the amplitudes of the current and voltage signals. Also, the amplitudes of the current and voltage signals may be determined by applying a computer algorithm to those signals after they have been digitized. The division process and subsequent signal conditioning may then be alternatively and equivalently accomplished by use of a digital computer. The remainder of the analog portion of the instant plethysmograph apparatus aspects are similar to known plethysmographs, such as that disclosed in U.S. Pat. No. 4,204,545.

The method of the present invention is accomplished as described aforesaid in connection with the stabilization and amplitude normalization of the exciter or oscillator utilized to apply the excitation current to the limb or body segment to be examined. In addition, a digital computer is utilized to select, average and analyze the individual volume pulsations, their first derivatives, and the total limb segment conductivity, together with a simultaneously obtained EKG signal. By storing and later averaging those signals over a plurality of beats, an improved signal-to-noise ratio and a more critical examination of the pulse wave profile is obtained.

Alternatively, any time varying physiologic signal which relates to the phasic volume changes to be measured and has identifiable characteristics occuring in fixed time relation to those phasic volume changes may be used in place of an EKG signal.

The method of the present invention produces an improved plethysmogram, and first and second derivatives of that plethysmogram, which provide an accurate indication of the pulsatile volume and net inflow present in the body segment under examination.

BRIEF DESCRIPTION OF THE DRAWINGS

FIG. 7 is a table, constructed by the computer, of the output provided by the periodic computerized measurement of the pulsatile volume and net inflow curves and includes a graphic representation of the former of those measurements.

DETAILED DESCRIPTION OF THE PREFERRED EMBODIMENT

Figure 1:
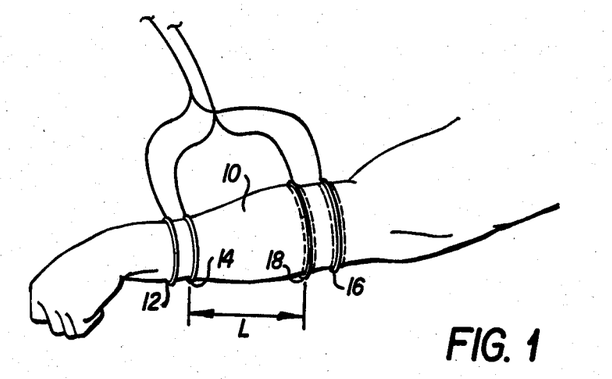
FIG. 1 shows a schematic diagram of the four electrodes positioned on a human limb.

Referring now in detail to the drawings where in like parts are designated by like reference numerals throughout, there is illustrated in FIG. 1 one of the peripheral limbs or body segments 10 of a human body, for example, the forearm. An electrical signal, of, for instance, 47 kilohertz at 1 milliamp of current, is applied to the forearm via two electrodes 12 and 16. The resultant voltage in the limb is measured between a second pair of electrodes 14 and 18 placed within the first pair of electrodes 12 and 16. The distance L between the inner electrodes 14 and 18 may be approximately 20 centimeters. All of the electrodes 12, 14, 16 and 18 may be of the circumferential type, and may consist of one-quarter inch aluminized mylar attached to an adhesive tape.

As will be discussed further herein, the two outer electrodes 12 and 16 may be capacitively coupled to the secondary of an isolation transformer 24, the primary of which is driven by a current source or oscillator 20, through a voltage-to-current converter 22. The two inner electrodes 14 and 18 may be capacitively coupled to the primary of a second isolation transformer 28. The secondary windings of that isolation transformer 28 are connected to an instrumentation amplifier 30. Each electrode 12, 14, 16 and 18 may be connected to its respective isolation transformers 24 and 28 through a 0.1 microfarad, 100 volt capacitor.

Figure 2:
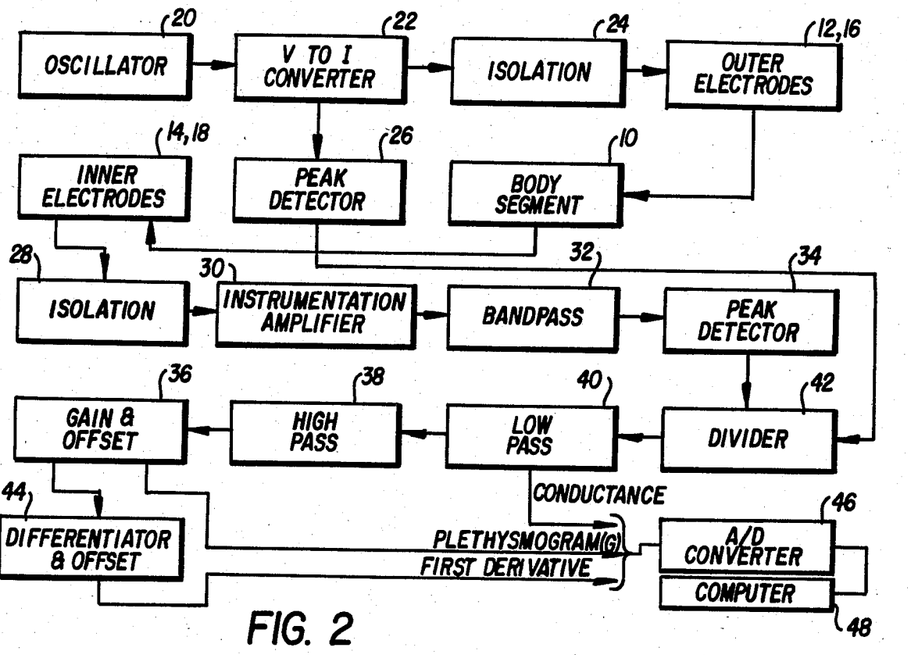
FIG. 2 is a block diagram illustrating a preferred embodiment of the peripheral limb blood flow measuring device of the present invention.
Figure 3:
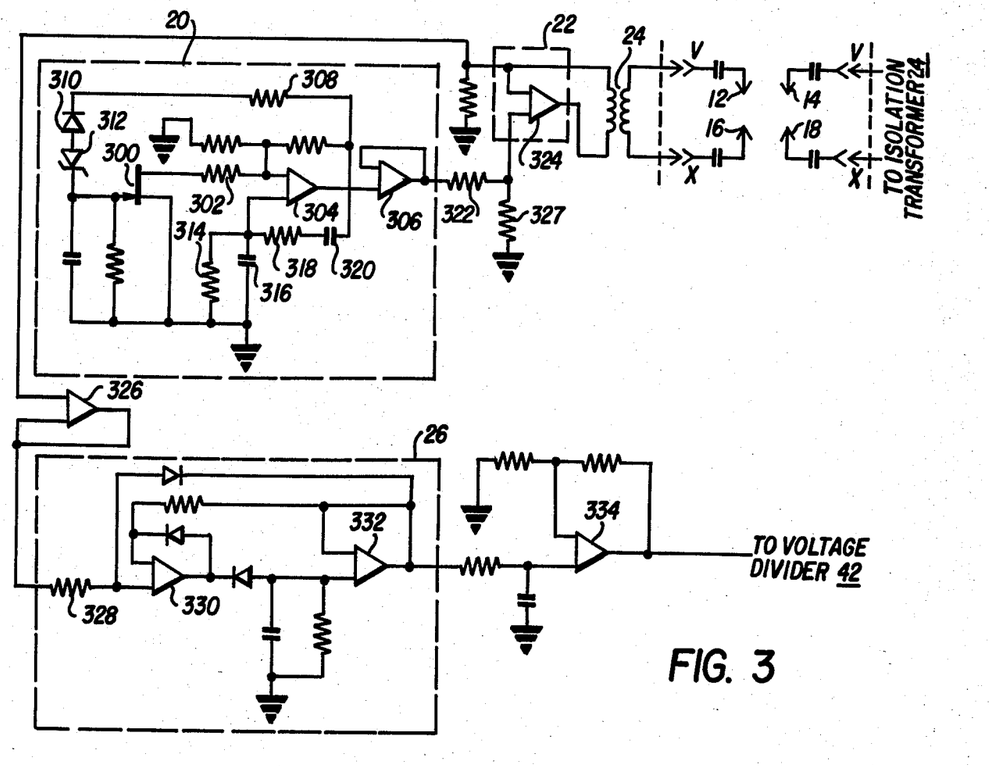
FIG. 3 is a schematic diagram of the electrical circuitry of the current source, isolation circuitry, and circuitry used to measure the amplitude of the current source utilized with the blood flow measuring device of FIG. 2.

Turning now to FIG. 2, there is shown therein, in block diagram form, a preferred embodiment of the admittance plethysmograph of the present invention. An oscillator 20, which may be a field effect transistor stabilized oscillator, is provided whose output is converted from a voltage to a current by means of converter 22. The output of the converter 22 is preferably a sine wave signal of frequency of 47 kilohertz and amplitude of 1 milliamp. A more detailed schematic diagram of the oscillator 20 and converter 22 is shown in FIG. 3.

The output from the converter 22 is fed through an isolation transformer 24, which may be a model SS031 available from TRW. As previously set forth, the outer patient electrodes 12 and 16 are connected to the secondary of that isolation transformer 24. The output from the inner patient electrodes 14 and 18 is connected to the primary of a second isolation transformer 28 which may be a model number SS041, also manufactured by TRW. The secondary windings of that isolation transformer 28 are connected to an instrumentation amplifier which may be, for instance, an operational amplifier manufactured by Analog Devices, model number AD521, of gain 100. The output from that instrumentation amplifer 30 may be fed to a bandpass filter 32 which is centered at the exciting oscillator's frequency (47 KHz in the preferred embodiment) and may have a Q value of 10. The output of the bandpass filter 32 is peak detected by detector 34 and fed to the denominator input of an analog divider 42. The analog divider 42 may preferably be a model number AD534 divider manufactured by Analog Devices.

A second peak detector 26 is connected to receive the current output from the converter 22 to detect the peak thereof. The output of that peak detector 26 is fed to the numerator input of the divider 42. Thus, the output signal from the body segment 10 of the patient, as measured across electrodes 14 and 18, is normalized by dividing the peak of the input current to the electrodes 12 and 16 by the peak of the output voltage measured across the electrodes 14 and 18. The peak detector 26, which in this embodiment is of the voltage clamping type, is shown in more detail in FIG. 3.

The output from the divider 42 is fed to a lowpass filter 40, which in this embodiment, is a 4th order Butterworth filter at 26 Hz to eliminate high frequency noise, and then to a highpass filter 38, which in this embodiment, is a 2nd order Butterworth filter at, 0.35 Hz, to extract the low magnitude phasic component of the tissue conductance. The output from the lowpass filter 40 is a voltage which is proportional to the total tissue conductance. The output from the highpass filter 38 is fed through a gain and offset circuit 36, which serves the purpose of offsetting and amplifying the low magnitude phasic component to a value which is suitable for A/D conversion as well as display on a device such as an oscilloscope and recording on a device such as a strip chart recorder. The output from the gain and offset circuit 36 is the admittance plethysmogram signal, which is representive of the pulse volume of the body segment 10.

The output from the gain and offset circuit 36 is fed to a differentiator and offset circuit 34 in order to generate the first derivative of the admittance plethysmogram signal. All three generated signals, namely the total conductance, admittance plethysmogram (or phasic conductance) and first derivative of the admittance plethysmogram signals may be fed to the input of an analog-to-digital converter 46 and then to a digital computer 48. The EKG from the patient (not shown) is also fed to the analog-to-digital converter 46 and then to the input of the digital computer 48. All of the circuitry set forth in FIG. 2, with the exception of the computer 48, may preferably be powered from a power supply which supplies plus and minus 15 volts DC. Such a power supply is manufactured, for example, by Polytron Devices, and is designated as model P-33.

Turning now to FIG. 3, a detailed circuit diagram of the oscillator 20, voltage-to-current converter 22 and peak detector 26 is shown therein. The oscillator 20 is based upon a field effect transistor 300, which may preferably be a model number REN 133, N-channel device. The drain of the FET 300 is connected through a resistor 302 to the inverting input of an operational amplifier 304. That operational amplifer may be a model number MC34004 manufactured by Motorola. The output of that operational amplifier 304 is fed to the non-inverting input of a similar operational amplifer 306, whose output is fed back to the inverting input of that operational amplifier 306. The output of the first operational amplifer 304 is fed through a resistor 308 to the cathode of a first diode 310, which may preferably a model number 1N914. The anode of that diode 310 is connected to the anode of a zener diode 312 which may preferably be a model number 1N4730, of 3.9 volt rating. The cathode of that second diode 312 is connected to the gate of the FET 300. The source of the FET 300 is connected to ground. The non-inverting input of the operational amplifier 304 is connected to ground through a resistor 314 and capacitor 316 and also to the output of that operational amplifer 304 through another resistor 318 and another capacitor 320. Thus, by appropriate selection of the values of the resistors and capacitors utilized in the oscillator circuit 20, an output of approximately 47 KHz is available at the output of the operational amplifer 306.

The output from that operational amplifer 306 is divided by a voltage divider consisting of resistors 322 and 327 and is then fed to the non-inverting input of a third operational amplifier 324, which functions as the primary element of the voltage-to-current converter 22. That operational amplifer may be preferably a model number MC34001 device also manufactured by Motorola. The output from operational amplifier 324 is fed to the primary coil of the isolation transformer 24. The other input of the operational amplifer 324 is connected to the other side of the primary winding of the isolation transformer 24 and also to the input of an operational amplifer 326 which may be a model number MC34004 device. The output of operational amplifer 326 is connected to its inverting input and functions as a buffer between the voltage-to-current converter 22 and peak dectector 26. The inverting input terminal of the operational amplifer 326 is connected through a resistor 328 to the first input of an operational amplifer 330. A second operational amplifer 332, which may be a model number MC34004, together with operational amplifier 330 functions as the peak detector 26. The output from that operational amplifer 332 is fed through a conditioning and gain circuit having as its primary operating device a similar operational amplier 334. The output from that operational amplifer 334 is fed to the analog divider 42.

Figure 4:
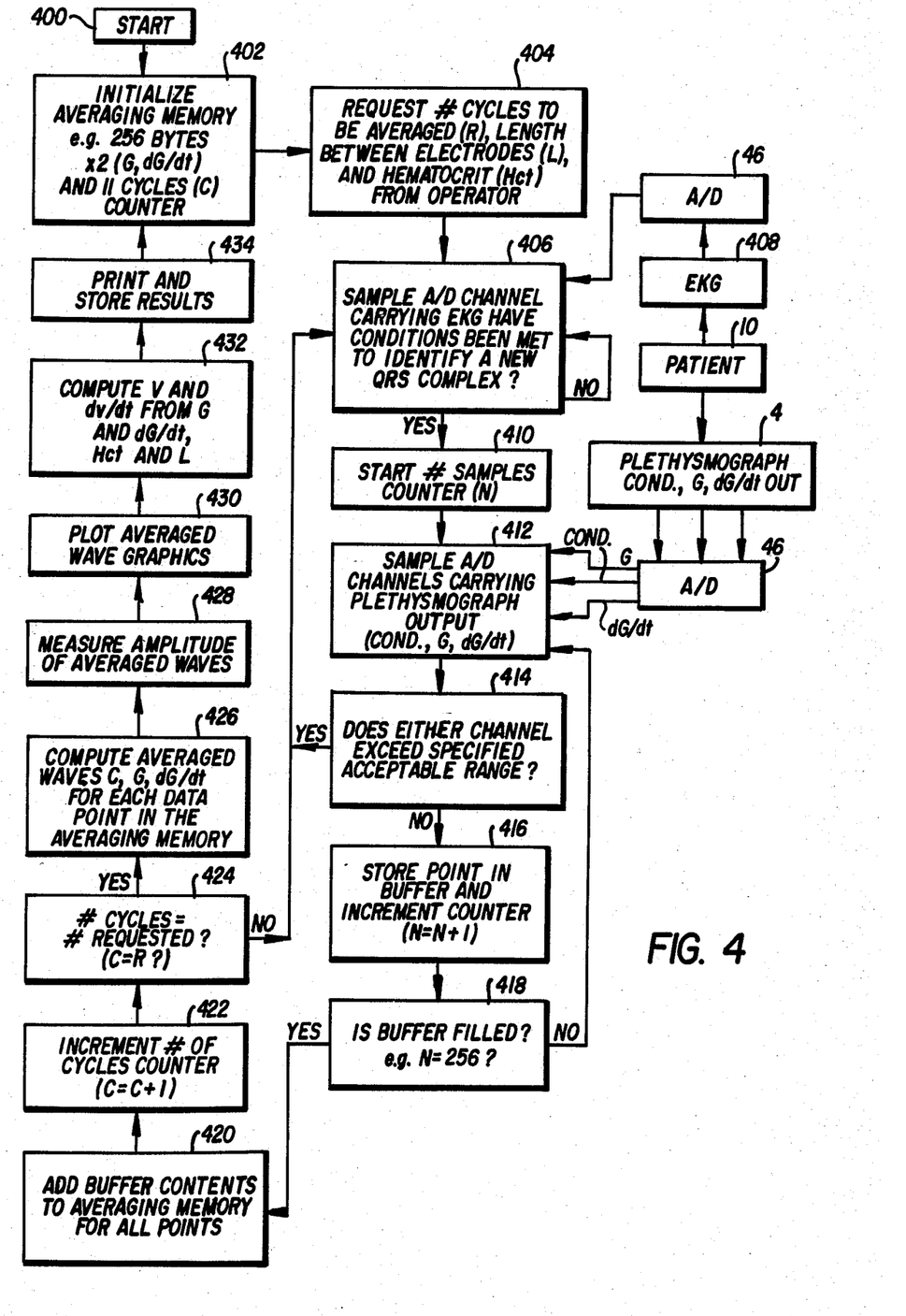
FIG. 4 is a block diagram of the flow chart of the program utilized by the digital computer as used in the present invention.

The conductance, admittance plethysmogram, first derivative and EKG signals may all be fed continuously to the analog-to-digital convertor 46. The program contained in the computer 48 is started 400 and the averaging memory is initialized 402. The program then requests the number of cycles to be averaged (R), the length between the electrodes (L) and the hematocrit (Hct) from the operator. After those values have been inputed into the computer 48, the computer samples the analog-to-digital converter channel which contains the EKG signal 408. If the proper conditions have been met to identify a new QRS complex, the program then starts the number of samples counter 410. If the proper conditions have not been met (e.g. if two sequential EKG channel values have not increased by a predetermined amount), to identify a new QRS complex, the computer then again samples the EKG 408 to determine if such conditions have been met.

After the number of samples counter has been started, the program samples 412 the analog-to-digital channels carrying the plethysmograph output 4. The program then determines whether any channel of the plethysmograph 4 output exceeds a predetermined acceptable range. If it does not, the program then stores those data points and incremants the counter by one 416. If the program determines that any of the channels exceeds the predetermined acceptable range, the program then resets and returns to sample and identify another EKG complex 406.

After the data points have been stored and the buffer and the counter incremented by one 406, the program determines whether the buffer is filled 418. If the buffer is not filled, the program again samples the A/D channels carrying the plethysmograph output 412. Thus, the program continues sampling until the entire buffer is filled. If it is determined that the buffer is filled 418, the program then adds the buffer contents to an averaging memory for all data points 420. The program then increments the number of cycles counter 422 and then determines whether the number of cycles is equivalent to the number of cycles requested 424. If not, the program returns to sample and identify another EKG complex 406. If the number of cycles is equivalent to the number of cycles requested, the program computes the averaged plethysmograph outputs for each data point in the averaging memory 426.

The program then measures the amplitude of the average values 428 and plots those average values 430 on a suitable output device (not shown). The program then identifies and computes the peak-to-peak value of the pulsatile volume curve, and the peak value of the first derivative of the pulsatile volume curve. It then converts those values into physiologic units (e.g. microliters and microliters per second respectively) from the aforementioned processed plethysmograph outputs, the hematocrit, and the length between electrodes values 432. Those values are then both printed on a suitable output device and also stored within the memory of the computer 434. The program then returns to initialize the averaging memory and number of cycles counter 402.

Figure 5:
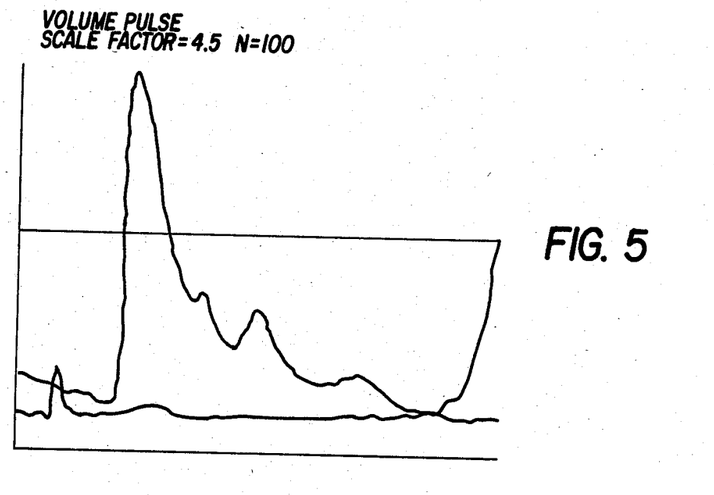
FIG. 5 is a graph of the volume pulse signal obtained by the present invention.
Figure 6:
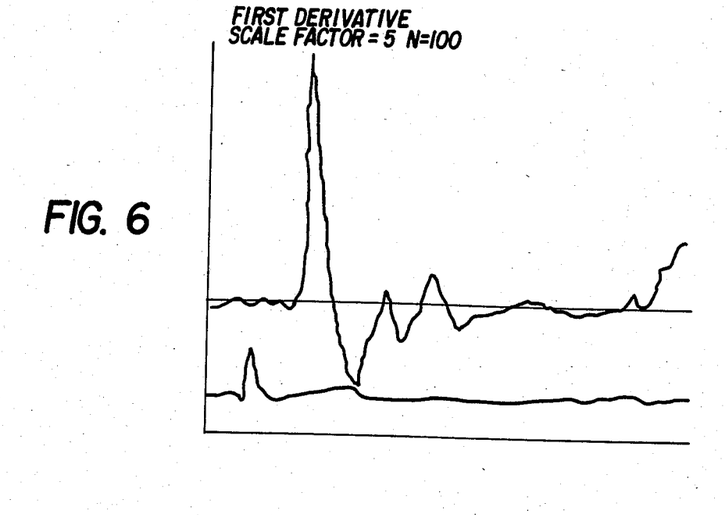
FIG. 6 shows a graph of the first derivative of the volume pulse signal, or the pulsatile net inflow, as obtained by the present invention.

The desired volume pulse graph is shown in FIG. 5. The first derivative of the graph of the volume pulse or the net inflow is shown in FIG. 6. The program may be recycled automatically to provide continuous measurements and/or graphic representation of pulsatile volume and net inflow as shown in FIG. 7. In that figure, the first column is a tabulation of sequential peak-to-peak pulsatile volume determinations, the second column is a tabulation of sequentional peak pulsatile net flow determinations, the third and fourth columns are the date and time respectively corresponding to the aforementioned determinations, and the fifth column is a graphic representation of the data contained in the second column, with larger values plotted toward the right and lower values toward the left. A valsalva maneuver (increase of intrathoracic pressure against a closed glottis), indicated at point A, is shown to decrease the pulsatile net flow and pulsatile volume transiently as does pressure upon the brachial artery, indicated at point B, of the forearm being measured in this demonstration.

In view of the foregoing, it should be apparent that there is provided by the present invention an admittance plethysmograph in which a high signal-to-noise ratio of the output signal measured from a body segment is achieved. In addition, by means of a digital computer, the outputs from the plethysmograph are analyzed and clarified such that the effects of the reduced signal-to-noise ratio are further enhanced.

Although only a preferred embodiment is specifically illustrated and described herein, it will be appreciated that many modifications and variations of the present invention are possible in light of the above teachings and within the purview of the appended claims without departing from the spirit and intended scope of the invention.

What I claim is:

1. A method of measuring the conductance and conductance changes in a body segment, comprising the steps of:
    applying an alternating current signal to said body segment;
    measuring the resulting voltage signal across said body segment caused by the application of said alternating current signal;
    producing a first signal corresponding to the magnitude of the alternating current signal and a second signal corresponding to the magnitude of the resulting voltage signal; and
    dividing said second signal by said first signal thereby producing a divided voltage signal,
    whereby the divided voltage signal is proportional to the conductance of said body segment.

2. A method of measuring the volume and volume changes in a body segment, comprising the steps of:
    applying an alternating current signal to on body segment;

measuring the resulting voltage signal across said body segment caused by the application of said alternating current signal;

producing a first signal corresponding to the magnitude of the alternating current signal and a second signal corresponding to the magnitude of the resulting voltage signal; and dividing said second signal by said first signal thereby producing a divided voltage signal, whereby the divided voltage signal is proportional to the volume of said body segment.

3. A method of measuring pulsatile volume of a fluid in a body segment, comprising the steps of:

applying an alternating current signal to said body segment;

measuring the resulting voltage signal across said body segment caused by the application of said alternating current signal;

producing a first signal corresponding to the magnitude of the alternating current signal and a second signal corresponding to the magnitude of the resulting voltage signal;

dividing said second signal by said first signal thereby producing a divided voltage signal; and filtering said divided voltage signal, whereby said filtered signal is proportional to the pulsatile volume of said fluid.

4. The method of claim 3, further including the step of differentiating said divided voltage signal, whereby said differentiated signal is proportional to the pulsatile net inflow of fluid in said body segment.

5. The method of claim 3, further including the steps of:

converting said filtered signal to a digitized volume signal;

generating a synchronous signal having an identifiable characteristic which occurs in a fixed time relationship with the generator of the pulsatile fluid flow;

converting said synchronous signal to a digitized synchronous signal;

locating in time an identifiable characteristic of said digitized synchronous signal; and sampling said digitized volume signal over a predetermined period of time beginning with said identifiable characteristic of said digitized synchronous signal, whereby the sampled digitized volume signal is representative of the pulsatile volume.

6. The method of claim 4, further including the steps of:

converting said filtered signal to a digitized volume signal;

converting said differentiated signal to a digitized net inflow signal;

generating a synchronous signal having an identifiable characteristic which occurs in a fixed time relationship with the generator of the pulsatile fluid flow;

converting said synchronous signal to a digitized synchronous signal;

locating in time an identifiable characteristic of said digitized synchronous signal; and sampling said digitized net inflow signal over a predetermined period of time beginning with said identifiable characteristic of said digitized synchronous signal, whereby the sampled digitized volume signal is representative of the pulsatile volume and the sampled digitized net inflow signal is representative of the pulsatile net inflow.

7. The method of claim 6, further including the steps of excluding from said sampling steps those digitized volume and digitized net inflow signals which fall outside of a predetermined range during said predetermined period of time.

8. The method of claim 7, further including the steps of:

repetitively sampling said digitized volume and net inflow signals for a predetermined plurality of cycles; and averaging such plurality of sampled digitized volume and net inflow signals to produce averaged pulsatile volume and pulsatile net inflow waveforms.

9. The method of claim 8, further including the step of measuring the amplitudes of said averaged pulsatile volume and pulsatile net inflow waveforms.

10. The method of claim 8, further including the step of identifying in time the peaks of said averaged pulsatile volume and pulsatile net inflow waveforms in relationship to said identifiable characteristics of said digitized synchronous signal.

11. A method of measuring at least one of the pulsatile volume and net inflow of a body segment using an electrical plethysmograph having a pulsatile volume signal and a net inflow signal as outputs, comprising:

converting said pulsatile volume signal to a digitized volume signal;

generating a synchronous signal having an identifiable characteristic which occurs in a fixed time arrangement with the generator of the pulsatile fluid flow;

converting said synchronous signal to a digitized synchronous signal;

locating in time an identifiable characteristic of said digitized synchronous signal; and sampling said digitized volume signal over a predetermined period of time beginning with said identifiable characteristic of said digitized synchronous signal.

12. The method of claim 11, further including the steps of:

converting said net inflow signal to a digitized net inflow signal; and sampling said digitized net inflow signal over a predetermined period of time beginning with said identifiable characteristic of said digitized synchronous signal, whereby the sampled digitized volume signal is representative of the pulsatile volume and the sampled digitized net inflow signal is representative of the pulsatile net inflow.

13. The method of claim 12, further including the step of excluding from said sampling steps those digitized volume and digitized net inflow signals which fall outside of a predetermined range during said predetermined period of time.

14. The method of claim 13, further including the steps of:

repetitively sampling said digitized volume and net inflow signals for a predetermined plurality of cycles; and averaging such plurality of sampled digitized volume and net inflow signals to produce averaged pulsatile volume and pulsatile net inflow waveforms.

15. The method of claim 14, further including the step of measuring the amplitudes of said averaged pulsatile volume and pulsatile net inflow waveforms.

16. The method of claim 14, further including the step of identifying in time the peaks of said averaged pulsatile volume and pulsatile net inflow waveforms in relationship to said identifiable characteristics of said digitized synchronous signal.

17. Apparatus for measuring the conductance and conductance change in a body segment, comprising:
   means for applying an alternating current signal to said body segment;
   means for measuring the resulting voltage signal across said body segment caused by the application of said alternating current signal;
   means for producing a first signal corresponding to the magnitude of the alternating current signal and a second signal corresponding to the magnitude of the resulting voltage signal; and
   means for dividing said second signal by said first signal thereby producing a divided voltage signal.

18. Apparatus for measuring the volume and volume changes in a body segment, comprising:
   means for applying an alternating current signal to said body segment;
   means for measuring the resulting voltage signal across said body segment caused by the application of said alternating current signal;
   means for producing a first signal corresponding to the magnitude of the alternating current signal and a second signal corresponding to the magnitude of the resulting voltage signal; and
   means for dividing said second signal by said first signal thereby producing a divided voltage signal.

19. Apparatus for measuring pulsatile volume of a fluid in a body segment, comprising:
   means for applying an alternating current signal to said body segment;
   means for measuring the resulting voltage signal across said body segment caused by the application of said alternating current signal;
   means for producing a first signal corresponding to the magnitude of the alternating current signal and a second signal corresponding to the magnitude of the resulting voltage signal;
   means for dividing said second signal by said first signal thereby producing a divided voltage signal; and
   means for filtering said divided voltage signal, whereby said filtered signal is proportional to the pulsatile volume of said fluid.

20. The apparatus of claim 19, further comprising means for differentiating said divided voltage signal, whereby said differentiated signal is proportional to the pulsatile net inflow of fluid in said body segment.

21. The apparatus of claim 19, further comprising:
   means for converting said filtered signal to a digitized volume signal;
   means for generating a synchronous signal having an identifiable characteristic which occurs in a fixed time relationship with the generator of the pulsatile fluid flow;
   means for converting said synchronous signal to a digitized synchronous signal;
   means for locating in time an identifiable characteristic of said digitized synchronous signal; and
   means for sampling said digitized volume signal over a predetermined period of time beginning with said identifiable characteristic of said digitized synchronous signal.

22. The apparatus of claim 20, further comprising:
   means for converting said filtered signal to a digitized volume signal;
   means for converting said differentiated signal to a digitized net inflow signal;
   means for generating a synchronous signal having an identifiable characteristic which occurs in a fixed time relationship with the generator of the pulsatile fluid flow;
   means for converting said synchronous signal to a digitized synchronous signal;
   means for locating in time an identifiable characteristic of said digitized synchronous signal; and
   means for sampling said digitized net inflow signal over a predetermined period of time beginning with said identifiable characteristic of said digitized synchronous signal.

23. The apparatus of claim 22, further comprising means for excluding from said sampling steps these digitized volume and digitized net inflow signals which fall outside of a predetermined range during said predetermined period of time.

24. The apparatus of claim 23, further comprising:
   means for repetitively sampling said digitized volume and net inflow signals for a predetermined plurality of cycles; and
   means for averaging such plurality of sampled digitized volume and net inflow signals to produce averaged pulsatile volume and pulsatile net inflow waveforms.

25. The apparatus of claim 24, further comprising means for measuring the amplitudes of said averaged pulsatile volume and pulsatile net inflow waveforms.

26. The apparatus of claim 24, further comprising means for identifying in time the peaks of said averaged pulsatile volume and pulsatile net inflow waveforms in relationship to said identifiable characteristics of said digitized synchronous signal.

27. Apparatus for measuring at least one of the pulsatile volume and net inflow of a body segment using an electrical plethysmograph having a pulsatile volume signal and a net inflow signal as outputs, comprising:
   means for converting said pulsatile volume signal to a digitized volume signal;
   means for generating a synchronous signal having an identifiable characteristic which occurs in a fixed time arrangement with the generator of the pulsatile fluid flow;
   means for converting said synchronous signal to a digitized synchronous signal;
   means for locating in time an identifiable characteristic of said digitized synchronous signal; and
   means for sampling said digitized volume signal over a predetermined period of time beginning with said identifiable characteristic of said digitized sychronous signal.

28. The method of claim 1, wherein said steps of producing a first signal corresponding to the magnitude of the alternating current signal and a second signal corresponding to the magnitude of the resulting voltage signal and dividing said second signal by said first signal are performed by a digital computer.

* * * * *